(12) United States Patent
 Hart (10) Patent No.: US 10,792,193 B2
(45) Date of Patent: *Oct. 6, 2020

(54) NASAL DRIP PAD

(71) Applicant: KAH MEDICAL SUPPLIES, LLC, Ashland, KY (US)

(72) Inventor: Karen Hart, Ashland, KY (US)

(73) Assignee: KAH MEDICAL SUPPLIES, LLC, Ashland, KY (US)

( * ) Notice: Subject to any disclaimer, the term of this patent is extended or adjusted under 35 U.S.C. 154(b) by 748 days.

This patent is subject to a terminal disclaimer.

(21) Appl. No.: 15/440,768

(22) Filed: Feb. 23, 2017

(65) Prior Publication Data
US 2017/0224539 A1   Aug. 10, 2017

Related U.S. Application Data

(63) Continuation-in-part of application No. 14/793,226, filed on Jul. 7, 2015, now Pat. No. 9,603,749.

(60) Provisional application No. 62/021,941, filed on Jul. 8, 2014.

(51) Int. Cl.
   *A61F 13/12*   (2006.01)
   *A61F 13/00*   (2006.01)
(52) U.S. Cl.
   CPC ...... *A61F 13/126* (2013.01); *A61F 13/00012* (2013.01); *A61F 13/00017* (2013.01); *A61F 13/00029* (2013.01); *A61F 13/00051* (2013.01)

(58) Field of Classification Search
   CPC .......... A61F 13/00029; A61F 13/00012; A61F 2013/00093; A61F 13/126; A61F 13/00085
   See application file for complete search history.

(56) References Cited

U.S. PATENT DOCUMENTS

| | | | | |
|---|---|---|---|---|
| 973,158 | A * | 10/1910 | Berthel | A61F 13/12 602/74 |
| 2,024,491 | A * | 12/1935 | Veysey | A61F 13/122 602/79 |
| 2,087,042 | A * | 7/1937 | Phillips | A61F 5/56 128/206.18 |
| 2,161,607 | A * | 6/1939 | Anderson | A62B 23/06 128/206.18 |
| 2,643,382 | A * | 6/1953 | McLeod | A61F 9/04 2/15 |
| 4,200,101 | A * | 4/1980 | Glassman | A61F 13/2051 604/385.18 |
| 4,774,935 | A * | 10/1988 | Aronsohn | A61F 5/30 128/97.1 |
| 5,284,469 | A * | 2/1994 | Jasen | A61F 13/126 128/858 |
| 5,312,324 | A * | 5/1994 | Walthour | A61F 13/126 128/206.18 |
| 6,768,040 | B1 * | 7/2004 | Sessions | A61F 13/126 128/206.11 |

(Continued)

*Primary Examiner* — Susan S Su
(74) *Attorney, Agent, or Firm* — King & Schickli, PLLC (57) ABSTRACT

A nasal drip pad apparatus for use on an individual. The apparatus includes a drip pad assembly positioned configured to be positioned underneath an individual's nose and a string forming configured to form a pair of loops. One of the loops is placed around one of the patient's ears and the other one of the loops is placed around the other one of the patient's ears.

19 Claims, 5 Drawing Sheets

(56) References Cited

U.S. PATENT DOCUMENTS

| | | | |
|---|---|---|---|
| 8,746,090 B2* | 6/2014 | Haveri | A61B 5/0878 |
| | | | 73/866.5 |
| 9,615,974 B1* | 4/2017 | Efobi | A61F 13/00085 |
| 2007/0079830 A1* | 4/2007 | Edwards, Jr. | A41D 13/1192 |
| | | | 128/205.27 |
| 2010/0106120 A1* | 4/2010 | Holm | A61F 13/068 |
| | | | 604/358 |
| 2010/0330140 A1* | 12/2010 | Stewart | A41D 13/11 |
| | | | 424/411 |
| 2016/0008179 A1* | 1/2016 | Hart | A61F 13/126 |
| | | | 604/377 |
| 2016/0296383 A1 | 10/2016 | Atkins et al. | |
| 2016/0367276 A1* | 12/2016 | Moloney | A61B 17/24 |
| 2018/0256403 A1* | 9/2018 | Lauer | A61F 17/00 |
| 2019/0183686 A1* | 6/2019 | Farrell | A61F 13/126 |
| 2019/0269183 A1* | 9/2019 | Qu | A41D 13/1161 |

* cited by examiner

NASAL DRIP PAD

This application is a continuation-in-part of U.S. patent application Ser. No. 14/793,226 filed on Jul. 7, 2015, which claims the benefit of U.S. Provisional Patent Application Ser. No. 62/021,941, filed on Jul. 8, 2014, the disclosure of which is incorporated herein by reference.

TECHNICAL FIELD

This disclosure relates generally to an apparatus for use with persons experiencing fluid discharge from their nose and, more particularly, to a nasal drip apparatus with an absorbent pad assembly for positioning underneath a patient's nose after sinus or nasal reconstructive surgery.

BACKGROUND

Generally, sinus surgery involves the removal of diseased sinus tissue with improvement in the natural drainage channels by the creation of a pathway for infected material to drain from the sinus cavities. In recent years, the surgeon will employ endoscopic techniques which allow better and more precise visualization without the need for external incisions. Endoscopic sinus surgery typically results in less swelling, bleeding, and discomfort, and a faster recovery from sinus surgery.

Endoscopic sinus surgery may be performed under local or general anesthesia. The procedure involves the use of a small telescope (nasal endoscope) that is inserted into the nasal cavity through the nostril to visualize your nose and sinuses. The primary goal of the surgery is to identify the narrow channels that connect the paranasal sinuses to the nasal cavity, enlarge these areas and improve the drainage from the sinuses into the nose.

Despite advances in sinus surgery, patients still suffer from certain post-operative conditions. For example, some patients may have noticeable swelling of the nose, upper lip, cheeks, or around the eyes for several days after surgery, which will gradually go away and is often treated with ice-packs.

In addition, moderate bleeding from the nose is common and will also gradually decrease. In order to address the bleeding, it is well known to use gauze dressing also known as a "mustache dressing." The dressing is used to collect blood and should be changed as needed. It is not unusual to change these dressings every hour during the first 24 hours after surgery.

In more detail, a nasal drip pad consisting of a medical gauze pad (such as a 2×2 or 4×4 inch cotton pad) is applied to the patient under the nostrils and held in place via an adhesive such as tape. Specifically, the adhesive is applied over the gauze pad and affixed directly to the patient's cheeks to hold the gauze directly under the patient's nostrils to collect blood and other fluid.

Although the use of gauze pad taped to a patient's face functions to collect the blood and other fluid from the patient, it suffers from certain disadvantages. For example, as the gauze pad or other fabric must be attached, such as via tape or adhesive to the patient's face, it is not a single all-in-one disposable dressing as they consist of multiple parts, which is less efficient. Moreover, some patients are allergic to certain adhesives and the adhesive may be irritating to the skin and can be uncomfortable to the patient as the adhesive is in direct contact with the patient's face. As the gauze pad collects fluid, it also must be periodically changed, which requires removing the adhesive from the patient's cheeks, which can add to the irritation and discomfort and is time-consuming. Furthermore, typically only the gauze pad is changed, so the apparatus is reused, which is not particularly sanitary and can lead to infections and the like.

Accordingly, there is a need for a more efficient, more comfortable and less cumbersome nasal drip pad to accommodate patients after sinus surgery or nasal reconstruction surgery. The improved nasal drip pad should increase the patient's comfort while wearing it and also allow the gauze to be more easily changed. Moreover, the improved nasal drip pad is primarily designed to be used as a single use application, which promotes sanitization and decreases the risk for infection.

SUMMARY

In accordance with one aspect of the disclosure, a nasal drip pad apparatus is disclosed. The apparatus includes a drip pad assembly configured to be positioned underneath a patient's nose and a string configured to form a pair of loops. One of the loops is placed around one of the patient's ears and the other one of the loops is placed around the other one of the patient's ears.

In one embodiment, the drip pad assembly includes a first pad and a second pad wherein the pads may be removably connected. The first pad may be a cylindrical-shaped non-woven fabric roll and the second pad may be a rectangular-shaped sheet of fabric gauze. The first and second pads may be made of a cotton fabric or made of two different materials. The string may form a continuous loop configured to extend through the interior of the drip pad assembly such that the first loop may be formed at a first end of the drip pad assembly and the second loop may be formed at an opposite end of the drip pad assembly.

In yet another aspect of the disclosure, a nasal drip pad apparatus for use on a post-operative sinus or nasal surgery patient is disclosed. The apparatus includes a drip pad assembly configured to be positioned underneath the patient's nose having two distinct layers. A first string is configured to create a first opening on one side of the drip pad assembly such that the first opening on the first side is configured to be positionable over one of the patient's ears and a second string is configured to create a second opening on an opposite side of the drip pad assembly such that the second opening on the opposite side is configured to be positionable over the other one of the patient's ears.

In one embodiment, the first and second strings are connected to the respective ends of the drip pad assembly via an adhesive or stitching. The second distinct layer may substantially cover the entirety of the first distinct layer and may further be removably connected to the first distinct layer. The first and second distinct layers of the drip pad assembly may form a circular cross-section. The first and second strings may be made from an elastic material. The first layer may be made of cotton material, while the second layer may be made from a cotton, rayon or nylon-type fabric. The drip pad apparatus may also include a third layer positioned on an exterior surface of the second layer. An adjuster may also be utilized for varying the size of the openings.

Another related aspect of this disclosure is an apparatus for use on a post-operative sinus or nasal surgery patient. The apparatus includes a body formed from a non-woven cotton roll surrounded by a cotton gauze pad and a string removably attached to an interior portion of the body for securing to the patient, wherein the removable attachment of the string to the interior portion of the body is in the absence of any adhesive or fasteners.

BRIEF DESCRIPTION OF THE DRAWINGS

The accompanying drawings and photographs incorporated in and forming a part of the specification, illustrate several aspects of this disclosure, and together with the description serve to explain the principles of the disclosure. In the drawings.

DETAILED DESCRIPTION

In the following detailed description, reference is made to the accompanying drawings that form a part hereof, and in which is shown by way of illustration, specific embodiments in which the invention may be practiced. These embodiments are described in sufficient detail to enable those skilled in the art to practice the embodiments and like numerals represent like details in the various figures. Also, it is to be understood that other embodiments may be utilized and that process or other changes may be made without departing from the scope of the disclosure. The following detailed description is not to be taken in a limiting sense, and the scope of the invention is defined only by the appended claims and their equivalents. In accordance with the disclosure, a nasal drip pad apparatus is hereinafter described.

Reference is now made to FIGS. 1-5, which are various views illustrating one embodiment of the nasal drip pad apparatus 10. Although the nasal drip pad apparatus 10 may be commonly used with patients (P) after post-sinus surgery, it should also be appreciated that the nasal drip pad apparatus 10 may have other uses. For example, a person may use the nasal drip pad apparatus 10 in conjunction with bloody or runny noses, especially if the skin near the nose is sensitive or inflamed from constantly using tissues for the fluid discharge from the nose. In addition, medical and dental professionals may use the nasal drip pad apparatus during procedures and/or treatment of patients for runny noses and other ailments to avoid constantly having to blow their nose into a tissue as well as to treat facial lacerations.

Figure 1:
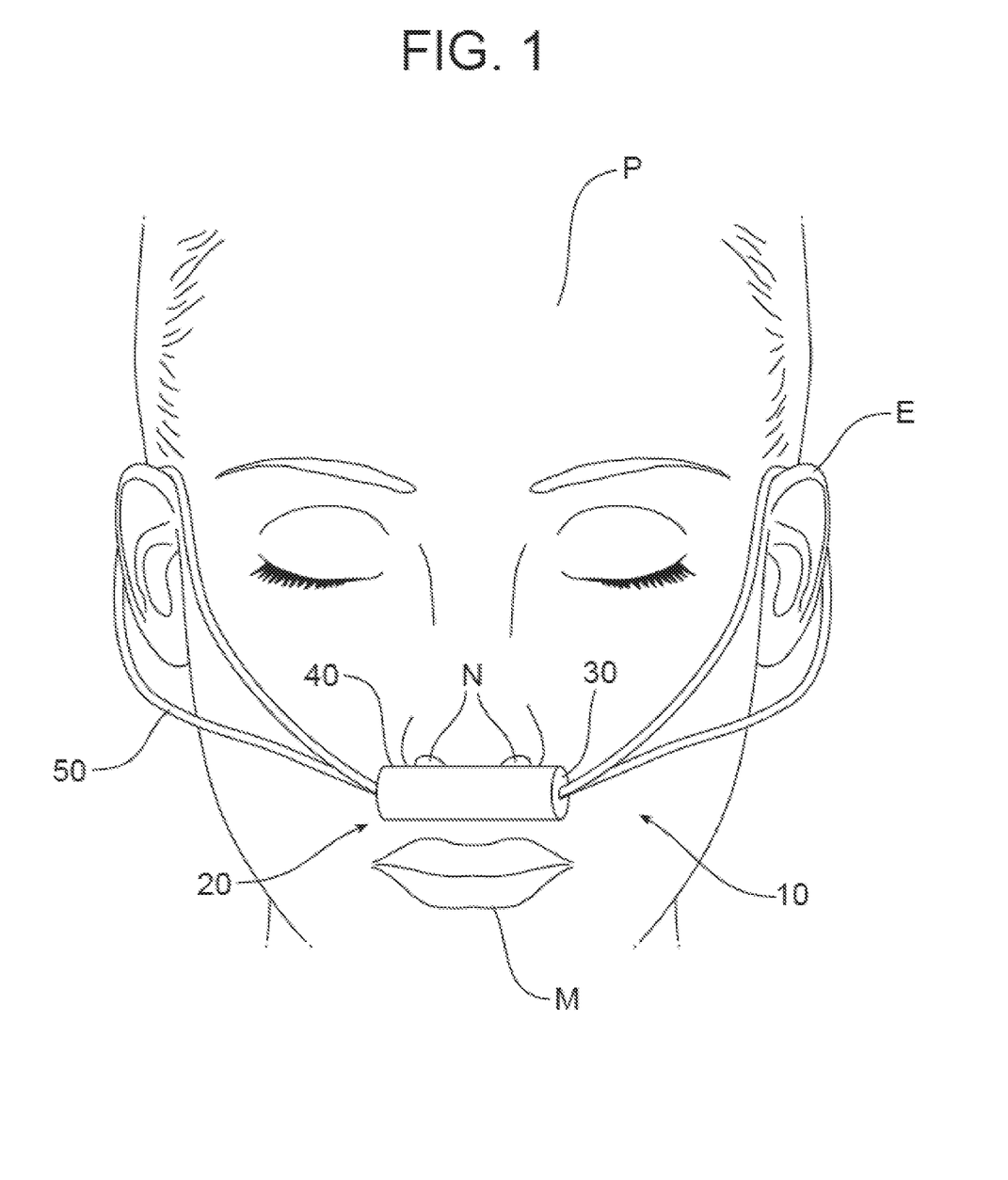
FIG. 1 is a front view of a nasal drip pad on a representative patient forming one aspect of this disclosure.
Figure 2:
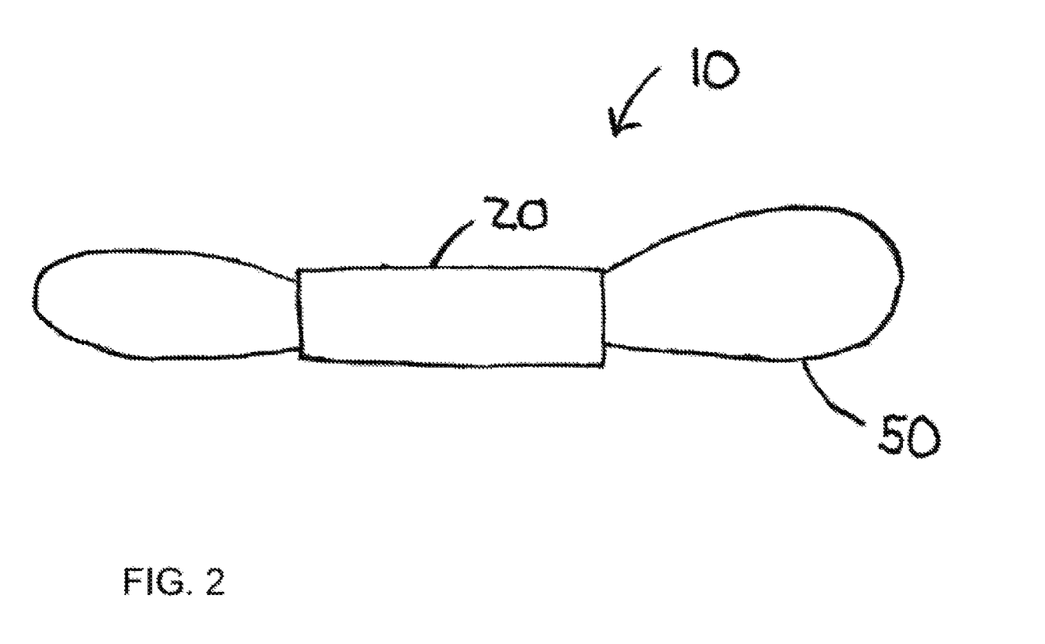
FIG. 2 is a front view of the nasal drip pad forming one aspect of this disclosure.

As shown in these FIGS. 1-4, the apparatus 10 includes a drip pad assembly or roll 20 made of an absorbent material, which is positioned directly underneath the patient's nostrils (N) and above the patient's mouth (M) (as best shown in FIG. 2). The absorbent material is typically made out of a cotton material, which is commonly used in medical, dental and first aid applications. As discussed below, the absorbent material used with the drip pad assembly 20 may be the same material or include more than one type of gauze or fabric.

Figure 3:
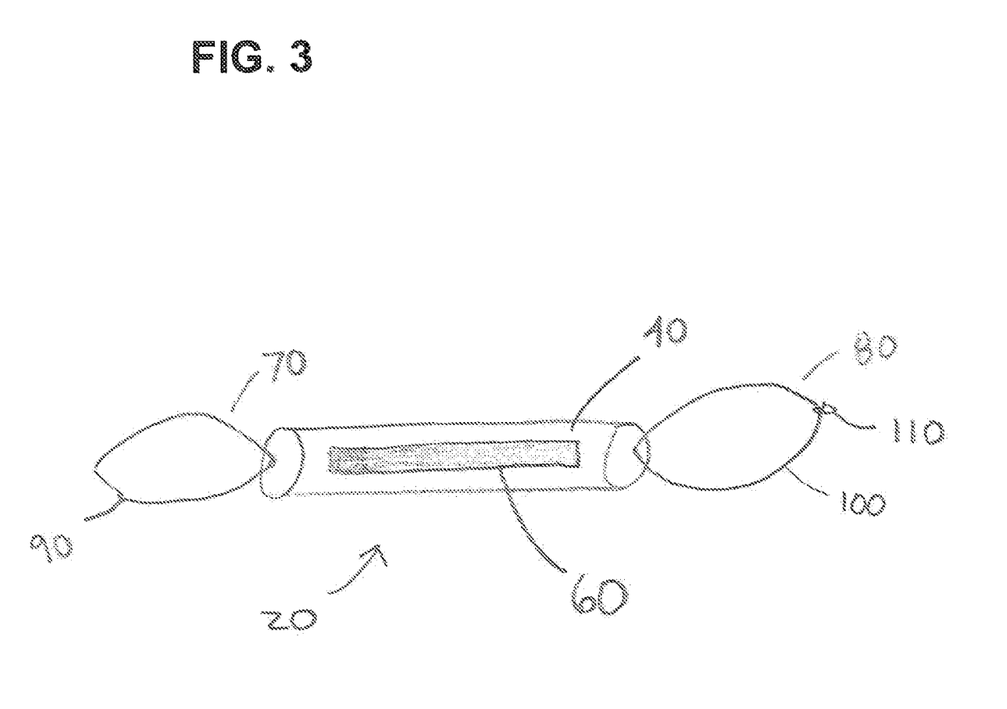
FIG. 3 is a front view of another embodiment of a nasal drip pad forming one aspect of this disclosure.
Figure 4:
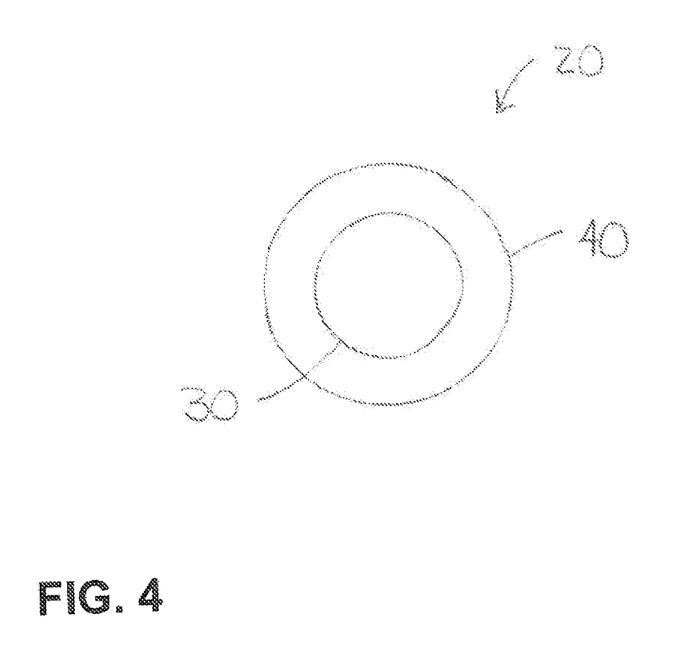
FIG. 4 is a cross-sectional view of a drip pad assembly (without a band, string or straps) used with the nasal drip pad forming one aspect of this disclosure.

As shown in FIG. 3, the drip pad assembly 20 includes an absorbent material containing two distinct cotton rolls or pads. A first pad or inner layer 30 may be a cylindrically-shaped absorbent roll. The absorbent material used in the first pad 30 is typically of the type used in dental applications, namely, a non-woven cotton dental roll that is often placed in a patient's mouth during dental procedures for its highly absorbent properties. The absorbent material is tightly compacted and highly absorbent so that the apparatus 10 does not have to be replaced as often as conventional drip pads. It should be appreciated that the first pad 30 may be made in different sizes to accommodate the patient's size and preference. In addition, a type of fluid-resistant material may be used with the first pad to reduce leakage to the exterior of the pad.

The first pad 30 is surrounded by a second pad or outer layer 40 such that only the opposite ends of the cylinder of the first pad are exposed. An adhesive, such as polyurethane glue may be used to aid in bonding the pads together. However, the adhesive is only used on the pads or rolls such that it does not contact the patient's face, which irritates the patient's skin and cause discomfort to the patient. The ends of the first pad 30 are intended to be exposed so that a strap, string or band 50 (discussed below) may be used with the drip pad assembly 20. The second pad 40 is typically a substantially rectangular or square-shaped gauze pad. The second pad may be made out of a soft fabric material, such as cotton, rayon or nylon-type fabric. The second pad 40 may also be made of yarn-like material to give the appearance of a braided effect, similar to a braided dental roll.

Typically, the second pad 40 is thinner than the first pad 30. The second pad 40 is also not as dense or tightly rolled as the first pad 30 as it is directly contacts the patient's face, i.e., underneath the patient's nose. As a result, the second pad is designed not only for its absorbent properties, but also to provide comfort to the patient that is not present in conventional drip pads. To this end, the second pad may removable and disposable such that it may be replaced by another similar pad to reduce the likelihood of infection caused by soiled material contacting the skin. As shown in FIG. 3, on the exterior of the second pad 40, an extra material or layer 60 such as a non-woven material may be bonded by heat or medical adhesive or stitched over the seam for increased durability.

On each side of the drip pad assembly 20, the strap, string or band 50 is connected to attach around the patient's ears to hold the absorbent material in place below the nostrils (as shown in FIGS. 1 and 2). It should be appreciated that the strap, string or band is typically made of a soft material that does not irritate the patient's face. For example, it may be made of elastic, non-elastic, cloth or other similar material such that it can properly fit around patients of different sizes. In one particular embodiment, the string 50 is made of a polyester material, which is beneficial for its strength, elasticity and resistance to shrinking as compared to other industrial fibers.

Figure 5:
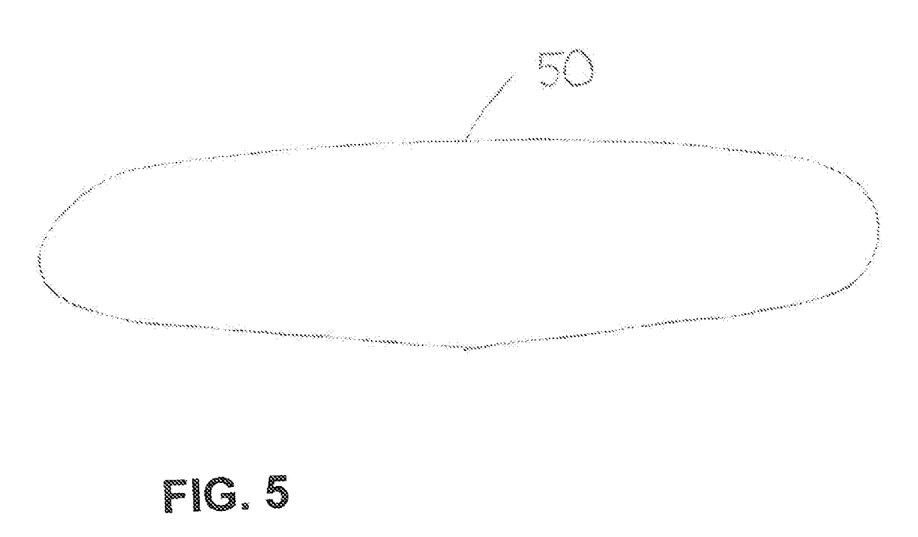
FIG. 5 is top view of the band or string used with the drip pad assembly forming one aspect of this disclosure.

Turning to FIG. 5, the string 50 may be a continuous loop, which is typically substantially permanently connected or affixed to the drip pad assembly 20 such that the string 50 cannot be removed without damaging the apparatus 10. In one embodiment, one end of the continuous loop of string 50 is removably slid through the interior of the drip pad assembly 20 such that a substantially circular or oval opening on each side of the drip pad is created. Each of these openings may be placed around the patient's ear (E) after sinus surgery. The apparatus is designed to be relatively loose fitting around the patient such that it does not cause any discomfort to the patient during use, but snug enough to keep the drip pad assembly 20 properly positioned between the patient's nose and mouth. Alternatively, instead of forming loops or openings on each side of the drip pad, Velcro material or hooks could be affixed to each end of the string. The string may be wrapped around each ear of the patient forming a loop and the Velcro or hooked-ends of the string could attach to the drip pad assembly or roll on the seam side.

The string 50 is typically adjustable such that either side of the string 50 may be pulled to make one of the loops bigger or smaller. When the drip pad assembly is ready to be replaced due to the amount of blood absorbed, the loops of the string 50 may be easily removed from around the patient's ears and replaced with another apparatus 10. The ear loops may move freely through the center of the roll with one end extending a continuous loop, while the other end has a cut loop, which may have an adjuster to allow for sizing or it may simply be tied around the patient's ear.

In another embodiment perhaps best shown in FIG. 3, the string 50 forming the ear loops is not continuous, but is two separate strings 70, 80. Each of the respective strings attaches to one of the opposed ends of the drip pad assembly 20. Each of the respective strings may attach to either the inner or outer layer of the drip pad assembly. Furthermore, each string is configured to form separate loops 90, 100 that may loop around a patient's ears to secure the assembly.

In yet another embodiment, the drip pad assembly 20 may be removably secured to the string or bands by fasteners or other suitable means. For example, the drip pad assembly may include hooks, which attach at a first end to the drip pad and at a second end to the string or band such that the string or band may be easily looped around the hook and then placed behind each of the patient's ears. Advantageously, due to the loose fitting, the apparatus 10 may be easily removed when the drip pad assembly 20 needs to be replaced. Advantageously, the string is adjustable to create a looser or snugger fit depending on the patient's preference. A cinch or adjuster 110 may be attached to one of the loops may be used to tighten the straps.

Advantageously, the nasal drip pad apparatus 10 disclosed herein is not as complex as most other drip pads known in the art as stitching or heating is not required. Moreover, the nasal drip pad apparatus is a unitary embodiment such that all the elements are connected, so there are not separate parts that may be lost or require assembly during use. Furthermore, it does not include the use of any adhesives, such as polyurethane glue applied directly to the patient's face, which can be burdensome for the patient. Finally, the nasal drip pad apparatus is easily adjustable and removable to facilitate the need to replace the drip pad and the patient's need for comfort. Unlike most other dressings and apparatus used for post-nasal surgery patients, the nasal drip pad apparatus 10 disclosed herein is intended to be a single use, all-in-one disposable dressing. Thus, once the nasal drip pad apparatus 10 performs its application, it may be easily removed and disposed and replaced with another nasal drip pad apparatus.

The foregoing descriptions of various embodiments have been presented for purposes of illustration and description. These descriptions are not intended to be exhaustive or to limit the invention to the precise forms disclosed. The embodiments described provide the best illustration of the inventive principles and their practical applications to thereby enable one of ordinary skill in the art to utilize the disclosure in various embodiments and with various modifications as are suited to the particular use contemplated.

The invention claimed is:

1. A nasal drip pad apparatus, comprising:
    a drip pad assembly configured to be positioned underneath a patient's nose; and
    a string configured to form a pair of loops,
    whereby one of the loops is configured to be placed around one of the patient's ears without extending around an entirety of the patient's head and the other one of the loops is configured to be placed around the other one of the patient's ears without extending around the entirety of the patient's head.

2. The nasal drip pad apparatus according to claim 1, wherein the drip pad assembly includes a first pad and a second pad.

3. The nasal drip pad apparatus according to claim 2, wherein the first and second pads are removably connected.

4. The nasal drip pad apparatus according to claim 2, wherein the first pad is a cylindrical-shaped non-woven fabric roll.

5. The nasal drip pad apparatus according to claim 2, wherein the second pad is a rectangular-shaped sheet of fabric gauze.

6. The nasal pad apparatus according to claim 2, wherein the first and second pads are made of a cotton fabric.

7. The nasal pad apparatus according to claim 2, wherein the first and second pads are made of two different materials.

8. The nasal pad apparatus according to claim 1, wherein the string forms a continuous loop configured to extend through the interior of the drip pad assembly such that a first loop is formed at a first end of the drip pad assembly and a second loop is formed at an opposite end of the drip pad assembly.

9. A nasal drip pad apparatus for use on a post-operative sinus or nasal surgery patient, comprising:
    a drip pad assembly configured to be positioned underneath a patient's nose, said drip pad assembly having first and second distinct layers, wherein the first distinct layer is surrounded by the second distinct layer such that only opposed ends of the first distinct layer are exposed;
    a first string configured to create a first opening on one side of the drip pad assembly such that the first opening on the first side is configured to be positionable over one of the patient's ears without extending around an entirety of the patient's head; and
    a second string configured to create a second opening on an opposite side of the drip pad assembly such that the second opening on the opposite side is configured to be positionable over the other one of the patient's ears without extending around the entirety of the patient's head.

10. The nasal pad according to claim 9, wherein the first and second strings are connected to the respective ends of the drip pad assembly via an adhesive.

11. The nasal pad according to claim 9, wherein the first and second strings are connected to the respective ends of the drip pad assembly via stitching.

12. The nasal drip pad apparatus according to claim 9, wherein the first and second distinct layers of the drip pad assembly form a circular cross-section.

13. The nasal drip pad apparatus according to claim 9, wherein the first and second strings are made from an elastic material.

14. The nasal drip pad apparatus according to claim 9, wherein the second distinct layer is removably connected to the first distinct layer.

15. The nasal drip pad apparatus according to claim 9, further comprising a third layer positioned on an exterior surface of the second distinct layer.

16. The nasal drip pad apparatus according to claim 9, wherein the first layer is made from a cotton material.

17. The nasal drip pad apparatus according to claim 9, wherein the second layer is made from a cotton, rayon or nylon-type fabric.

18. The nasal drip apparatus according to claim 9, further comprising at least one adjuster for varying the size of the openings.

19. An apparatus for use on a post-operative sinus or nasal surgery patient, comprising:
   a body formed from a non-woven cotton roll surrounded by a cotton gauze pad; and
   a string removably attached to an interior portion of the body configured for securing over the patient's ears such that the string does not extend around an entirety of the patient's head, wherein the removable attachment of the string to the interior portion of the body is in the absence of any adhesive or fasteners.

\* \* \* \* \*